(12) United States Patent
Yoon et al.

(10) Patent No.: US 9,040,740 B2
(45) Date of Patent: May 26, 2015

(54) METHOD FOR PREPARING ALKYL LACTATE AND A METHOD FOR PREPARING LACTAMIDE USING THE SAME

(75) Inventors: Sung-Cheol Yoon, Daejeon (KR); Seung-Young Park, Daejeon (KR); In-Su Lee, Seoul (KR)

(73) Assignee: LG Chem, Ltd., Seoul (KR)

( * ) Notice: Subject to any disclaimer, the term of this patent is extended or adjusted under 35 U.S.C. 154(b) by 54 days.

(21) Appl. No.: 13/642,760

(22) PCT Filed: May 17, 2011

(86) PCT No.: PCT/KR2011/003633
§ 371 (c)(1),
(2), (4) Date: Dec. 5, 2012

(87) PCT Pub. No.: WO2011/145867
PCT Pub. Date: Nov. 24, 2011

(65) Prior Publication Data
US 2013/0079547 A1   Mar. 28, 2013

(30) Foreign Application Priority Data
May 18, 2010   (KR) .................. 10-2010-0046625

(51) Int. Cl.
*C07C 69/68*   (2006.01)
*C07C 233/00*   (2006.01)
*C07C 67/40*   (2006.01)
*C07C 231/02*   (2006.01)

(52) U.S. Cl.
CPC .............. *C07C 67/40* (2013.01); *C07C 231/02* (2013.01)
USPC ........................................ 560/179; 564/123

(58) Field of Classification Search
USPC ........................................ 560/179; 564/123
See application file for complete search history.

(56) References Cited

U.S. PATENT DOCUMENTS

| 2009/0088589 A1 | 4/2009 | Enomoto et al. |
| 2010/0047140 A1 | 2/2010 | Enomoto et al. |

FOREIGN PATENT DOCUMENTS

| CN | 1564801 | 1/2005 |
| CN | 101492367 | 7/2009 |
| EP | 0523 014 A2 | 1/1993 |
| KR | 10-2009-0106992 | 10/2009 |
| WO | WO 2005/072132 | 8/2005 |
| WO | WO 2007/001043 | 1/2007 |
| WO | WO 2009/121488 | 10/2009 |
| WO | WO 2009/121489 | 10/2009 |

OTHER PUBLICATIONS

Wang et al, STN CAPLUS abstract, Shipin Keji (2006).*
Yang et al. "Acyl transfer catalysis with 1,2,4-Triazole Anion", Org Lett, vol. 11, No. 7, pp. 1499-1502, Apr. 2, 2009.*
Shen et al. "Effect of Alkaline catalysts on hydrothermal conversion of glycerin into lactic acid", Ind. Eng. Chem. Res., vol. 48, pp. 8920-8925, 2009.
Maris et al. "Glycerol hydrogenolysis on carbon-supported PtRu and AuRu bimetallic catalysts", Journal of Catalysis, vol. 251, pp. 281-294, 2007.
Kishida et al. "Conversion of glycerin into lactic acid by alkaline hydrothermal reaction", Chemistry Letters, vol. 34, No. 11, pp. 1560-1561, 2005.
Maris et al. "Hydrogenolysis of glycerol over carbon-supported Ru and Pt catalysts", Journal of Catalysis, vol. 249, pp. 328-337, 2007.
"Cyclic Guanidine Organic Catalyst; What Is Magic About Triazabicyclodecene" Kiesewetter, et al; J Org. Chem 2009, 74 (24), 9490-9496.
"Acyl Transfer Catalysis with 1, 2, 4-Triazole Anion"; Yang, et al.; Organic Letters, 2009, 11(7) 1499-1502,
Esben Taarning, et al. "Oxidation of glycerol and propanediols in methanol over heterogeneous gold catalysts" Green Chemistry, vol. 10, No. 4, Jan. 1, 2008, p. 408, XP055157922, ISSN: 1463-9262, DOI:.

* cited by examiner

*Primary Examiner* — Kamal Saeed
*Assistant Examiner* — Janet L Coppins
(74) *Attorney, Agent, or Firm* — McKenna Long & Aldridge, LLP

(57) ABSTRACT

This disclosure relates to a method for preparing alkyl lactate with high yield and high selectivity, comprising the step of reacting glycerol with water or alcohol in the presence of a catalyst.

In addition, the present invention provides a method for efficiently preparing lactamide using the alkyl lactate.

6 Claims, No Drawings

METHOD FOR PREPARING ALKYL LACTATE AND A METHOD FOR PREPARING LACTAMIDE USING THE SAME

This application is a National Stage Entry of International Application No. PCT/KR2011/003633, filed May 17, 2011, and claims the benefit of Korean Application No. 10-2010-0046625, filed on Mar. 18, 2010, which are hereby incorporated by reference in its entirety for all purposes as if fully set forth herein.

FIELD OF THE INVENTION

The present invention relates to a method for preparing alkyl lactate, more specifically a method for preparing alkyl lactate and a method for preparing lactamide using the same, which may prepare alkyl lactate with high yield, and then, efficiently prepare lactamide using the same.

BACKGROUND OF THE INVENTION

Recently, due to demand of biodiesel, a large quantity of glycerol is being produced, and studies on the application thereof are progressed.

Among them, preparation of lactic acid using glycerol has been suggested. For example, a method of preparing lactic acid from glycerol under sever conditions of 300° C., 80 atm through a hydrothermal reaction using alkali base such as NaOH, KOH is known (U.S. Patent Application Publication No. 2009/0088589; U.S. Patent Application Publication No. 2010/0047140; Ind. Eng. Chem. Res. 2009, 28, 8920; Chemistry letters 2005, 34, 1560).

However, this method has disadvantages in that an additional process for separating a catalyst is required because the catalyst is dissolved in the product due to the use of a homogeneous catalyst such as NaOH, KOH, and a large quantity of impurities are produced. Furthermore, since the catalyst separation process is very complicated and difficult, operability is lowered and the process is uneconomical in terms of the cost.

To solve the problems according to the use of a homogeneous catalyst, a method of preparing lactic acid through hydrogenation of glycerol using an active carbon-supported heterogeneous catalyst such as Pt, Ru, Au is known. However, this method also has disadvantages of low conversion rate and selectivity (Journal of catalyst 2007, 249, 328; Journal of catalyst 2007, 251, 281).

Meanwhile, in a stripper (stripping solution) for removing a photoresist layer in the manufacture process of fine circuit of semiconductor integrated circuit and liquid display device, NMP(N-methylpyrrolidone), DMAc(dimethyl acetamide), and the like are generally used as a solvent. However, since the solvent is highly toxic, lactamide compounds have been used as a solvent replacing the NMP, DMAc for operability and environmental-friendliness (Korean Laid-open Patent Publication No. 2009-0106992).

The lactamide compound is an environmentally-friendly low-toxic biosolvent based on biomass obtainable using glycerol that is by-product of the biodiesel. Thus, a method of increasing productivity of the lactamide compounds is being studied.

As the existing method of preparing lactamide, a method of preparing lactamide by reacting lactic acid, alkyl lactate with amines is known (WO 2009/121488, WO 2009/121489). However, when lactamide is prepared from lactic acid, lactic acid and alkyl lactate are obtained with low yield due to the above problems, and thus, yield and purity of lactamide may not be improved. Moreover, a method of preparing alkyl lactate with high yield and high purity has not been known.

DETAILED DESCRIPTION OF THE INVENTION

Technical Problem

The inventors confirmed that if alkyl lactate is prepared from glycerol and then, lactamide is prepared using the same, a catalyst separation process may be easily progressed, and conversion rate and selectivity may be largely improved.

Accordingly, the present invention provides a method for preparing alkyl lactate through dehydrogenation of glycerol and alcohol, oxidation and esterification in the presence of a catalyst.

In addition, the present invention provides a method for preparing lactamide with improved yield and purity, by the reaction with amine using the alkyl lactate as an intermediate.

Technical Solution

The present invention provides a method for preparing alkyl lactate of the following Chemical Formula 1, comprising the step of reacting glycerol with alcohol of the following Chemical Formula 2 in the presence of a catalyst:

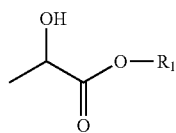

[Chemical Formula 1]

 $R_1OH$    [Chemical Formula 2]

wherein, $R_1$ is a substituted or unsubstituted C1-10 alkyl, a substituted or unsubstituted C3-10 cycloalkyl, a substituted or unsubstituted C6-10 aryl, a substituted or unsubstituted C3-10 alkylene, a substituted or unsubstituted C3-10 cycloalkylene, or a substituted or unsubstituted C6-10 arylene.

The catalyst may be a homogeneous or heterogeneous catalyst.

In addition, the alkyl lactate may be used as an intermediate for preparing lactamide of the following Chemical Formula 3.

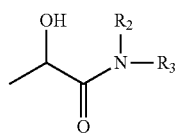

[Chemical Formula 3]

wherein $R_2$ and $R_3$ are independently hydrogen, substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene.

Thus, the present invention provides a method for preparing lactamide of the following Chemical Formula 3, comprising the step of reacting alkyl lactate of the following Chemical Formula 1 with dialkylamine of the following Chemical Formula 4:

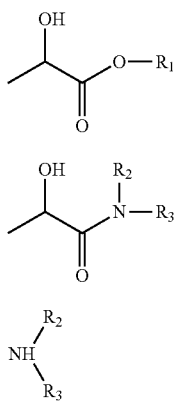

[Chemical Formula 1]

[Chemical Formula 3]

[Chemical Formula 4]

wherein, $R_1$ is substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene, and $R_2$ and $R_3$ are independently hydrogen, substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene.

The present invention will be explained in detail.

The present invention relates to a method of preparing alkyl lactate from glycerol, and then, preparing lactamide using the same as an intermediate, instead of preparing lactamide using lactic acid prepared from glycerol. Thus, according to the present invention, a catalyst separation process is simple compared to the existing method even if any catalyst of a homogeneous or heterogeneous catalyst is used, and conversion rate and selectivity to the product may be improved.

Namely, the present invention may prepare alkyl lactate using inexpensive glycerol as starting material, and then, prepare lactamide that is useful for a biosolvent by the reaction with amine compounds with high yield.

The method of the present invention first prepares an intermediate of alkyl lactate through dehydrogenation, oxidation and esterification, as shown in the Reaction Formula 1.

[Reaction Formula 1]

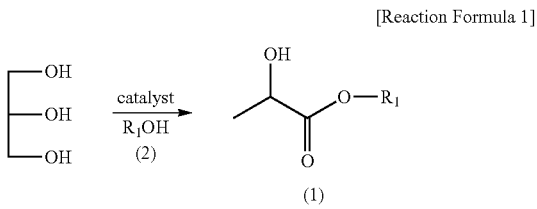

wherein, $R_1$ is substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene, As shown in the Reaction Formula 1, the present invention provides a method for preparing alkyl lactate of the following Chemical Formula 1, comprising the step of reacting glycerol with alcohol of the following Chemical Formula 2, in the presence of a catalyst:

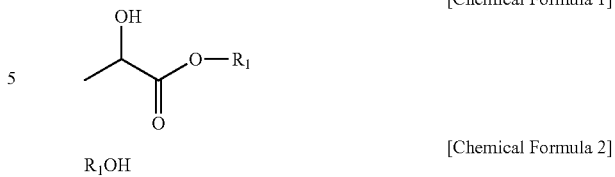

[Chemical Formula 1]

$R_1OH$      [Chemical Formula 2]

wherein, $R_1$ is a substituted or unsubstituted C1-10 alkyl, a substituted or unsubstituted C3-10 cycloalkyl, a substituted or unsubstituted C6-10 aryl, a substituted or unsubstituted C3-10 alkylene, a substituted or unsubstituted C3-10 cycloalkylene, or a substituted or unsubstituted C6-10 arylene.

As the glycerol, commonly available glycerol that is obtained as by-product of biodiesel may be used.

The alcohol of the Chemical Formula 2 may be used as a solvent and a reactant, and the content may be about 1 to 50 parts by weight, more preferably about 1 to 30 parts by weight, most preferably about 1 to 20 parts by weight, based on 1 part by weight of glycerol. If the content is less than about 1 part by weight, it may be difficult to sufficiently participate in the reaction, and if the content is greater than about 50 parts by weight, reaction pressure may be increased by the alcohol.

In addition, $R_1$ in the alcohol of the Chemical Formula 2 may be preferably methyl or ethyl.

Particularly, according to the present invention, since limitation according to the use of a catalyst may be minimized, any catalyst of a homogeneous or heterogeneous catalyst may be used as the catalyst. The existing method mainly used water as a solvent, but it was very difficult to separate lactic acid in the aqueous solution. To the contrary, since the preparation method of alkyl lactate of the present invention prepares alkyl lactate using alcohol, the catalyst may be easily separated and purified from the product after the reaction is completed even if any catalyst of a homogeneous or heterogeneous catalyst is used, and thereby, a process of separating a catalyst from the product may be easily progressed. The heterogeneous catalyst may be more advantageous because it may be more easily separated and recycled compared to the homogeneous catalyst.

As the homogeneous catalyst, at least one selected from the group consisting of an alkali metal compound having a hydroxyl group or an alkoxy group, a bicarbonate ($HCO_3^-$)-containing metal compound, and a carbonate ($CO_3^{2-}$)-containing metal compound may be used. The alkali metal compound having a hydroxyl group may include NaOH, KOH, LiOH, $Ba(OH)_2$, and the like. The alkali metal compound having an alkoxy group may include NaOR, KOR, LiOR, and the like (R is a substituted or unsubstituted C1-10 alkyl group). R may be methyl, ethyl, propyl or isopropyl.

As the heterogeneous catalyst, a metal compound containing Mg, Ca, Zr, Sn or Ti may be used.

In addition, the heterogeneous catalyst may be in the form of a complex of the metal compound containing Mg, Ca, Zr, Sn, Ti of an oxide form and other materials.

Preferably, the heterogeneous catalyst may further include at least one selected from the group consisting of an alkali metal compound, a hydroxyl group ($OH^-$)-containing metal compound, a bicarbonate ($HCO_3^-$)-containing metal compound, a carbonate ($CO_3^{2-}$)-containing metal compound, activated clay (acid clay), zeolite, active carbon, diatomaceous earth, bentonite, alumina, silicalite, fly ashes, molecular sieve, vermiculite, perlite, π-complex compound adsorbent, clay and polymer resin.

For example, the method for preparing alkyl lactate using the heterogeneous catalyst may be progressed using a heterogeneous catalyst of the metal compound containing Mg, Ca, Zr, Sn or Ti, and a hydroxyl group (OH—)-containing basic compound, and using an alcohol solvent.

The amount of the catalyst is not specifically limited, but it may be preferably about 0.001 to 10 equivalents, more preferably about 0.01 to 5 equivalents, based on 1 equivalent of glycerol.

Also, the reaction for preparing alkyl lactate may be conducted in a batch reactor or tubular reactor.

The reaction may be conducted at a temperature of about 100 to 300° C., preferably about 80 to 250° C., and a pressure of about 100 to 200 atm for about 1 to 20 hours under inert atmosphere. The inert atmosphere refers to common conditions such as Ar, helium, and the like.

According to the method, alkyl lactate may be prepared with yield of about 50% or more, preferably yield of about 70 to 90%, and selectivity of about 80% or more. In addition, since the method of the present invention uses alcohol as a solvent, separation and purification is easier compared to the existing method, and thus, effective alkyl lactate preparation method may be provided.

Further, the alkyl lactate may be used as an intermediate for preparing lactamide of the following Chemical Formula 3. Since the method of the present invention uses the alkyl lactate with high yield and high selectivity prepared according to the Reaction Formula 1 as an intermediate, lactamide may also be prepared with high yield and conversion rate may be improved.

Therefore, according to the present invention, lactamide of the following Chemical Formula 3 may be prepared by reacting alkyl lactate of the Chemical Formula 1 with dialkylamine of the following Chemical Formula 4, as shown in the following Reaction Formula 2.

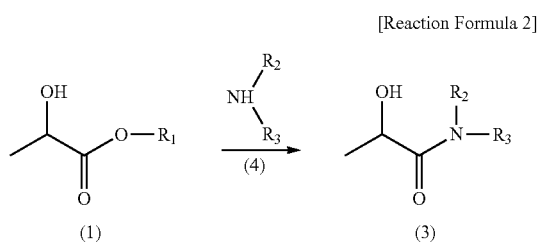

[Reaction Formula 2]

wherein, $R_1$ is substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene, and $R_2$ and $R_3$ are independently hydrogen, substituted or unsubstituted C1-10 alkyl, substituted or unsubstituted C3-10 cycloalkyl, substituted or unsubstituted C6-10 aryl, substituted or unsubstituted C3-10 alkylene, substituted or unsubstituted C3-10 cycloalkylene, or substituted or unsubstituted C6-10 arylene.

The reaction for preparing lactamide may be conducted at a temperature of about 0 to 150° C. for about 1 to 20 hours, preferably at a temperature of about 10 to 100° C. for about 3 to 20 hours. In addition, the dialkylamine of the Chemical Formula 4 may be used in the amount of about 1 to 5 equivalents, more preferably about 1 to 3 equivalents, based on 1 equivalent of the alkyl lactate of the Chemical Formula 1.

Furthermore, the reaction may be progressed under non-solvent or a C1-4 alcohol solvent, and the kind of the solvent is not specifically limited.

By this process, the present invention may efficiently provide lactamide with high yield and high purity compared to the existing method.

Advantageous Effects

According to the present invention, by preparing alkyl lactate from glycerol using a homogeneous or heterogeneous catalyst, and then, preparing lactamide using the same, an economical preparation method that has high yield and high selectivity and may easily separate and purify the catalyst by the use of glycerol may be provided.

Therefore, since the present invention may replace the existing expensive solvent and toxic NMP, DMAc, it is economical and environmentally friendly. In addition, since the present invention economically prepares alkyl lactate and lactamide that are used for monomer and raw material for preparing polymer, it may largely contribute to various fields including an electronic material preparation process, a coating solvent, an environmentally friendly field, and the like.

EXAMPLES

Hereinafter, the present invention will be explained in detail with reference to the following Examples. However, these examples are only to illustrate the invention, and the scope of the invention is not limited thereto.

Experiment Method

In the following Examples and Comparative Examples, all operations handling compounds sensitive to the air or water were conducted using standard Schlenk technique or dry box technique.

The conversion rates of the prepared alkyl lactate and lactamide were measured using GC (gas chromatography) and HPLC (High performance liquid chromatography).

Synthesis Example 1

Na/MgO Catalyst

80~85 wt % of Mg(OH)$_2$ and 15~20 wt % of NaOH were impregnated at 80° C. under carbon dioxide atmosphere, and dried at 125° C. And then, the mixture was fired at 850° C. for 4 hours, and a Na/MgO catalyst was obtained with yield of 90%.

Synthesis Example 2

Sn/zeolite Catalyst

Tetraethylorthosilicate (6 g), tetraethylorthotitanate (0.5 g), tin ethoxide (0.5 g) and tetrapropylammonium hydroxide (4 g, 40 wt %) were mixed in a high pressure reactor and the mixture was agitated at room temperature for 1 hour. The formed alcohol was removed by distillation, distilled water was added to the residue, and then, the mixture was crystallized at 175° C. for 24 hours under agitation. And then, the product was obtained through spray drying with yield of 94% based on SiO$_2$.

Synthesis Example 3

Na/NaOH/Al$_2$O$_3$ Catalyst

Al$_2$O$_3$ (80 wt %) and NaOH (10 wt %) were agitated at 550~600° C. for 4 hours, Na (10 wt %) was added, and the mixture was agitated for 1~2 hours, and then, cooled to room temperature to prepare a catalyst with yield of 85%.

Example 1

Preparation of Methyl Lactate Using the Catalyst 1

Glycerol (1 g), the catalyst 1 (0.2 g) and methanol (5 g) were introduced into a 200 mL high pressure reactor under Ar atmosphere, and reacted at 160° C. and 40 atm for 5 hours. And then, the reaction mixture was cooled to room temperature, and then, methyl lactate was separated by fractional distillation and obtained with 80% yield.

$^1$H NMR (CDCl$_3$): δ 4.3 (q), 3.79 (s), 2.89 (br s), 1.42 (d)

Example 2

Preparation of Methyl Lactate Using the Catalyst 2

Glycerol (1 g), the catalyst 2 (0.2 g) and methanol (5 g) were introduced into a 200 mL high pressure reactor under Ar atmosphere, and reacted at 160° C. and 40 atm for 5 hours. And then, the reaction mixture was cooled to room temperature, and methyl lactate was separated by fractional distillation and obtained with 90% yield.

$^1$H NMR (CDCl$_3$): δ 4.3 (q), 3.79 (s), 2.89 (br s), 1.42 (d)

Example 3

Preparation of Methyl Lactate Using the Catalyst 3

Glycerol (1 g), the catalyst 3 (0.2 g) and methanol (5 g) were introduced into a 200 mL high pressure reactor under Ar atmosphere, and reacted at 160° C. and 40 atm for 5 hours. And then, the reaction mixture was cooled to room temperature, and methyl lactate was separated by fractional distillation and obtained with 85% yield.

$^1$H NMR (CDCl$_3$): δ 4.3 (q), 3.79 (s), 2.89 (br s), 1.42 (d)

Example 4

Preparation of Methyl Lactate Using MgO

Glycerol (1 g), methanol (5 g), and MgO (0.2 g) and NaOH (0.5 g) as catalyst were introduced into a 200 mL high pressure reactor under Ar atmosphere, and reacted 160° C. and 40 atm for 5 hours. And then, the reaction mixture was cooled to room temperature, and methyl lactate was separated by fractional distillation and obtained with 93% yield.

$^1$H NMR (CDCl$_3$): δ 4.3 (q), 3.79 (s), 2.89 (br s), 1.42 (d)

Example 5

Preparation of Methyl Lactate Using CaO

Glycerol (1 g), methanol (5 g), and CaO (0.2 g) and NaOH (0.5 g) as catalyst were introduced into a 200 mL high pressure reactor under Ar atmosphere, and reacted 160° C. and 40 atm for 5 hours. And then, the reaction mixture was cooled to room temperature, and methyl lactate was separated by fractional distillation and obtained with 90% yield.

$^1$H NMR (CDCl$_3$): δ 4.3 (q), 3.79 (s), 2.89 (br s), 1.42 (d)

Example 6

Preparation of Methyl Lactate Using ZnO

Glycerol (1 g), methanol (5 g), and ZnO (0.2 g) and NaOH (0.5 g) as catalyst were introduced into a 200 mL high pressure reactor under Ar atmosphere, and reacted 160° C. and 40 atm for 5 hours. And then, the reaction mixture was cooled to room temperature, and methyl lactate was separated by fractional distillation and obtained with 88% yield.

$^1$H NMR (CDCl$_3$): δ 4.3 (q), 3.79 (s), 2.89 (br s), 1.42 (d)

Example 7

Preparation of Ethyl Lactate Using MgO

Glycerol (1 g), ethanol (5 g), and MgO (0.2 g) and NaOH (0.5 g) as catalyst were introduced into a 200 mL high pressure reactor under Ar atmosphere, and reacted 160° C. and 40 atm for 5 hours. And then, the reaction mixture was cooled to room temperature, and ethyl lactate was separated by fractional distillation and obtained with 90% yield.

$^1$H NMR (CDCl$_3$): δ 4.3 (q), 4.19 (q), 2.89 (br s), 1.42 (d), 1.33 (t)

Example 8

Preparation of N,N-dimethyl lactamide

Methyl lactate (4.5 g) obtained by the method of Examples 1~6, N,N-dimethylamine (4 g) and methanol (2 g) were introduced into a reactor at 0° C. under Ar atmosphere, the temperature was increased to 60° C., and the mixture was reacted for 20 hours. And then, the reaction mixture was cooled to room temperature, and N,N-dimethyl lactamide was obtained by fractional distillation (5.1 g, yield 60%).

$^1$H NMR (CDCl$_3$): δ 4.47 (q), 3.02 (s), 3.00 (s), 1.33 (d)

Example 9

Preparation of N,N-dimethyl lactamide

Ethyl lactate (1.5 g) obtained by Example 7 and N,N-dimethylamine (1 g) were introduced into a reactor at room temperature under Ar atmosphere, the temperature was increased to 80° C., and the mixture was reacted for 20 hours. And then, the reaction mixture was cooled to room temperature, and N,N-dimethyl lactamide was obtained by fractional distillation (1.3 g, yield 52%).

$^1$H NMR (CDCl$_3$): δ 4.47 (q), 3.02 (s), 3.00 (s), 1.33 (d)

Example 10

Preparation of N,N-dibutyl lactamide

Methyl lactate (1 g) obtained by the method of Examples 1~6, N,N-dibutyl amine (1.5 g) and methanol (2 g) were introduced into a reactor at 0° C. under Ar atmosphere, the temperature was increased to 60° C., and the mixture was reacted for 20 hours. And then, the reaction mixture was cooled to room temperature, and N,N-dibutyl lactamide was obtained by fractional distillation (0.9 g, yield 64%).

$^1$H NMR (CDCl$_3$): δ 4.47 (q), 3.27 (t), 1.59 (m), 1.36 (m), 1.03 (t)

Example 11

Methyl lactate was prepared with 73% yield by the same method as Example 1, except using NaOMe (0.5 g) as a catalyst.
$^1$H NMR (CDCl$_3$): δ 4.3 (q), 3.79 (s), 2.89 (br s), 1.42 (d)

Example 12

Methyl lactate was prepared with 65% yield by the same method as Example 1, except using NaOH (0.5 g) and H$_2$O (0.1 g) as a catalyst.
$^1$H NMR (CDCl$_3$): δ 4.3 (q), 3.79 (s), 2.89 (br s), 1.42 (d)

Example 13

Methyl lactate (4.5) obtained by Example 11, N,N-dimethylamine (4 g) and methanol (2 g) were introduced into a reactor at 0° C. under Ar atmosphere, the temperature was increased to 60° C., and then, the mixture was reacted for 20 hours. And then, the reaction mixture was cooled to room temperature, and N,N-dimethyl lactamide was obtained by fractional distillation (5.0 g, yield 59%).
$^1$H NMR (CDCl$_3$): δ 4.47 (q), 3.02 (s), 3.00 (s), 1.33 (d)

Comparative Example 1

Using 2 mL of NaOH (1.5M) as a catalyst and 2 mL of glycerol, a hydrothermal reaction was conducted under severe conditions of 300° C., 90 atm, and neutralization reaction was conducted with H$_2$SO$_4$, and then, lactic acid was prepared in an aqueous solution with 58% yield. The production of lactic acid was confirmed by LC (liquid chromathography).

Comparative Example 2

Lactic acid (1 g) obtained in Comparative Example 1 and N,N-dimethyl amine (1.5 g) were reacted at 160° C. for 16 hours to prepare N,N-methyl lactamide with 45% yield.
$^1$H NMR (CDCl$_3$): δ 4.47 (q), 3.02 (s), 3.00 (s), 1.33 (d)

The invention claimed is:

1. A method for preparing lactate compound of the following Chemical Formula 1, comprising the step of reacting glycerol with alcohol of the following Chemical Formula 2 in the presence of a catalyst, wherein the catalyst is a homogeneous or heterogeneous catalyst, wherein the homogeneous catalyst is at least one selected from the group consisting of an alkali metal compound having a hydroxyl or alkoxy group, a bicarbonate (HCO$_3^-$)-containing metal compound, and a carbonate (CO$_3^{2-}$)-containing metal compound, and wherein the heterogeneous catalyst is a metal compound containing Mg, Ca, Zr, Sn or Ti:

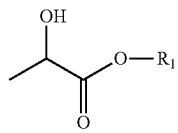
[Chemical Formula 1]

R$_1$OH
[Chemical Formula 2]

wherein, R$_1$ is a substituted or unsubstituted C1-10 alkyl, a substituted or unsubstituted C3-10 cycloalkyl, a substituted or unsubstituted C6-10 aryl, a substituted or unsubstituted C3-10 alkylene, a substituted or unsubstituted C3-10 cycloalkylene, or a substituted or unsubstituted C6-10 arylene.

2. The method according to claim 1, wherein the alkali metal compound having a hydroxyl group is NaOH, KOH, LiOH or Ba(OH)$_2$, and
the alkali metal compound having an alkoxy group is NaOR, KOR or LiOR (wherein, R is a substituted or unsubstituted C1-10 alkyl group).

3. The method according to claim 1, wherein the heterogeneous catalyst further comprises at least one selected from the group consisting of an alkali metal compound, a hydroxyl group-containing metal compound, a bicarbonate-containing metal compound, a carbonate-containing metal compound, activated clay, zeolite, active carbon, diatomaceous earth, bentonite, alumina, silicalite, fly ashes, molecular sieve, vermiculite, perlite, π-complex compound adsorbent, clay and polymer resin.

4. The method according to claim 1, wherein the reaction is conducted in a batch reactor or tubular reactor.

5. The method according to claim 1, wherein the reaction is conducted at a temperature of 100 to 300° C. and a pressure of 10 to 200 atm for 1 to 20 hours, under inert atmosphere.

6. The method according to claim 1, wherein R$_1$ in the alcohol of the Chemical Formula 2 is methyl or ethyl.

* * * * *